United States Patent [19]

Saita et al.

[11] Patent Number: 5,030,474

[45] Date of Patent: Jul. 9, 1991

[54] METHOD FOR FORMING HYDROXYAPATITE COATING FILM USING COATING LIQUOR CONTAINING HYDROXYAPATITE

[75] Inventors: Kenji Saita, Toyonaka; Shinji Fujiwara, Takatsuki, both of Japan

[73] Assignee: Sumitomo Chemical Company, Limited, Osaka

[21] Appl. No.: 576,166

[22] Filed: Aug. 31, 1990

Related U.S. Application Data

[63] Continuation of Ser. No. 289,313, Dec. 23, 1988, abandoned.

[30] Foreign Application Priority Data

Dec. 23, 1987 [JP] Japan .................................. 62-327727
Aug. 26, 1988 [JP] Japan .................................. 62-212708

[51] Int. Cl.$^5$ ...................... C23C 20/00; C23C 20/06; A61F 2/28
[52] U.S. Cl. ................................... 427/2; 427/376.1; 427/427; 623/16
[58] Field of Search ................ 427/2, 376.1, 427; 623/16

[56] References Cited

U.S. PATENT DOCUMENTS

| | | | |
|---|---|---|---|
| 4,366,183 | 12/1982 | Ghommidh et al. | 427/2 |
| 4,623,553 | 11/1983 | Ries et al. | 427/2 |
| 4,702,930 | 10/1987 | Heide et al. | 427/2 |
| 4,705,694 | 11/1987 | Buttazzoni et al. | 427/2 |
| 4,794,023 | 12/1988 | Shimamune et al. | 427/376.1 |
| 4,847,163 | 7/1989 | Shimamune et al. | 427/2 |

FOREIGN PATENT DOCUMENTS

| | | |
|---|---|---|
| 518908 | 1/1979 | Australia . |
| 52-82893 | 7/1977 | Japan . |
| 53-118411 | 10/1978 | Japan . |
| 53-128190 | 11/1978 | Japan . |
| 58-109049 | 6/1983 | Japan . |
| 59-111753 | 6/1984 | Japan . |

Primary Examiner—Shrive Beck
Assistant Examiner—Margaret Burke
Attorney, Agent, or Firm—Birch, Stewart, Kolasch & Birch.

[57] ABSTRACT

A method for forming a hydroxyapatite coating film on a surface of a substrate which comprises coating a coating liquor onto a surface of a substrate, followed by drying and then subjecting to insolubilization (e.g., treating with an insolubilizing agent or calcination) which is characterized by using a coating liquor comprising a colloidal dispersion of hydroxyapatite having a fine particle size of 0.5 μm or less.

6 Claims, 1 Drawing Sheet

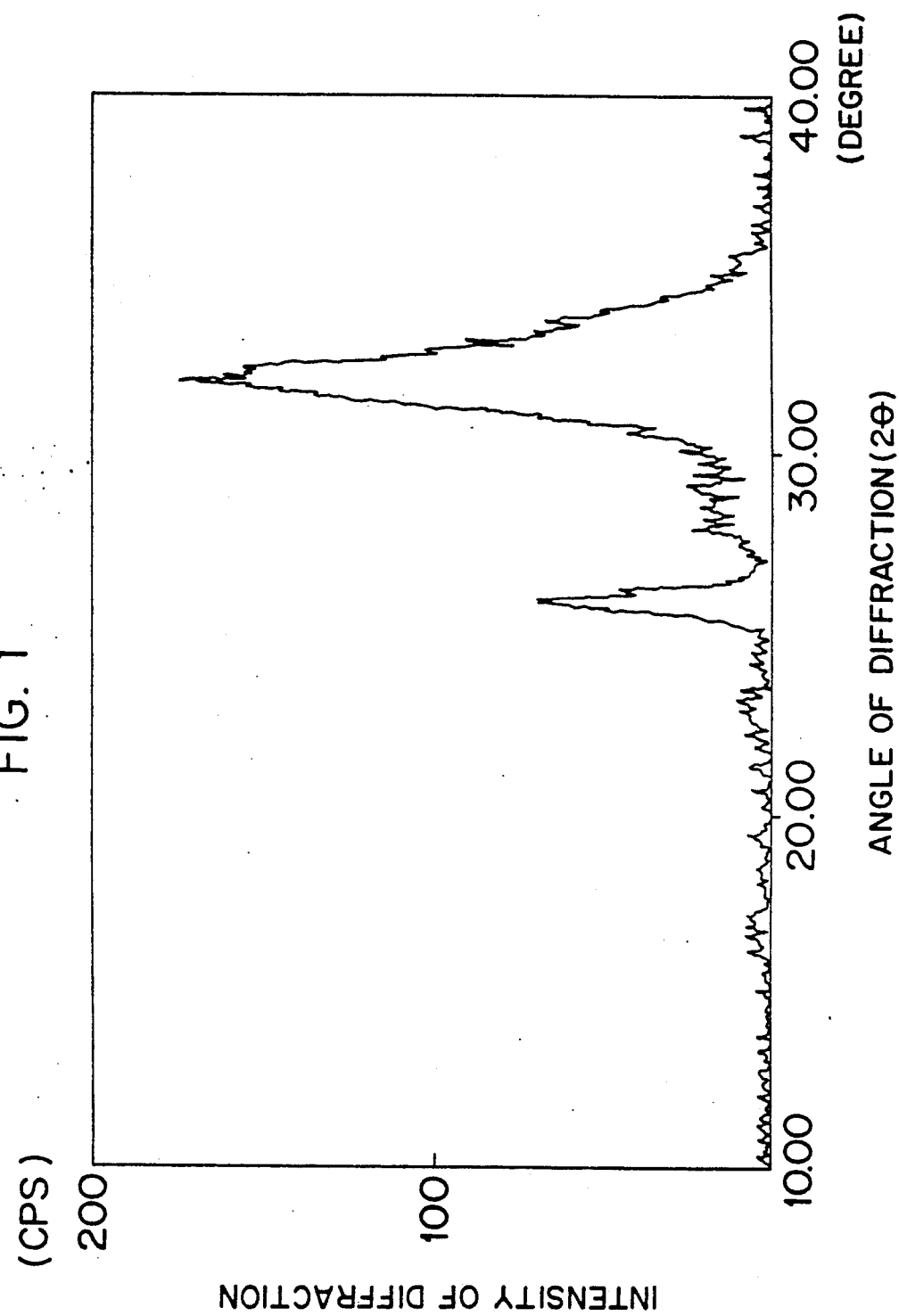

METHOD FOR FORMING HYDROXYAPATITE COATING FILM USING COATING LIQUOR CONTAINING HYDROXYAPATITE

This application is a continuation of application Ser. No. 289,313 filed on Dec. 23, 1988, now abandoned.

TECHNICAL FIELD

This invention relates to a coating liquor containing hydroxyapatite and a method for forming a hydroxyapatite coating film on a surface of a substrate by using the same. More particularly, it relates to a coating liquor comprising a colloidal dispersion of hydroxyapatite and a method for forming a hydroxyapatite coating film on a surface of a substrate by coating the coating liquor onto a surface of a substrate, followed by drying and then subjecting to insolubilization.

TECHNICAL BACKGROUND AND PRIOR ART

Hydroxyapatite has excellent affinity to living body and excellent adsorptivity and hence have been studied as to utilities thereof in a variety of fields, particularly use thereof as implants for replacing or repairing hard tissues of living bodies. The implants require to have a biodynamic strength in addition to the affinity to living body. Nevertheless, hydroxyapatite is not satisfactory in terms of the strength even in the form of a sintered product. Accordingly, from the practical viewpoint, it is favorable to use a substrate or core material such as metallic materials, ceramics, glass, etc. and to form a hydroxyapatite coating film on the surface of said substrate or core material.

Various methods have hitherto been proposed for forming a hydroxyapatite coating film, for example, a thermal plasma spray method (cf. Japanese Patent First Publication (Kokai) No. 82893/1977), a spattering method (cf. Japanese Patent First Publication (Kokai) No. 109049/1983), a physical vapor deposition (PVD) or chemical vapor deposition (CVD) method (cf. Japanese Patent First Publication (Kokai) No. 111753/1984), an electrophoretic method (cf. Japanese Patent First Publication (Kokai) No. 128190/1978), a coating method (cf. Japanese Patent First Publication (Kokai) No. 118411/1978).

However, the thermal plasma spray method, spattering method, CVD method and PVD method are hardly applied to a substrate having a complicated shape, for example, onto the inner surface of porous substrate, and the electrophoretic method can not form the coating film onto a substrate having no electrical conductivity. On the other hand, the coating method is advantageously easy in the treatment, and the above-mentioned Japanese Patent First Publication (Kokai) No. 118411/1978 discloses a method for forming a coating film by suspending fine particles of apatite in water and coating the aqueous suspension onto the surface of a substrate, followed by calcining the coated layer. However, this coating method has still a problem that it is usually difficult to prepare very fine particles and the particles are easily agglomerated, and further, the particles dispersed in water have usually a particle size of more than 0.5 $\mu$m, and hence, the apatite has less adhesion force to the substrate surface and the coating film is easily peeled off from the substrate.

SUMMARY DESCRIPTION OF THE INVENTION

Under the circumstances, the present inventors have intensively studied as to improved method for forming a hydroxyapatite coating film onto a substrate by a coating method and have found that in order to form a coating film having a high adhesion force by the coating method, it is necessary to coat a colloidal dispersion of hydroxyapatite having a very fine particle in a size as small as 0.5 $\mu$m or less in the state of forming no agglomeration of the particles, and further that when the thickness of the coated hydroxyapatite film is small as less than 2 $\mu$m, any cracking of the film does not occur. The present inventors have further studied and have found that when the thickness of coating film is large as more than 2 $\mu$m, the coating film is sometimes peeled off, but a part of the coating film remains on all of the peeled surface of the substrate and still strongly adheres to the substrate. Based on these new findings, it has been found that the desired hydroxyapatite coating film having good properties can be formed by using a specific coating liquor comprising a colloidal dispersion of hydroxyapatite.

An object of the invention is to provide a coating liquour comprising a colloidal dispersion of hydroxyapatite having a very fine particle size. Another object of the invention is to provide a method for forming a hydroxy-apatite coating film having excellent properties onto the surface of a substrate by a coating method. A further object of the invention is to provide an improved method for forming a hydroxyapatite coating film having excellent adhesion force and excellent strength onto the surface of a substrate which is useful in various fields. A still further object of the invention is to provide a method for forming a hydroxyapatite coating film on the surface of a substrate by using a specific colloidal dispersion of hydroxyapatite. These and other objects and advantages of the invention will be apparent to those skilled in the art from the following description.

BRIEF DESCRIPTION OF THE DRAWING

FIG. 1 shows a powder X-ray diffraction pattern of the product prepared by agglomerating the hydrosol and separating by filtration and then air-drying as prepared in Example 1 of this invention.

DETAILED DESCRIPTION OF THE INVENTION

The coating liquor of this invention comprises a colloidal dispersion of hydroxyapatite having a particle size of 0.5 $\mu$m or less. Further the method for forming a hydroxyapatite coating film of this invention comprises coating a colloidal dispersion of hydroxyapatite having a particle size of 0.5 $\mu$m or less onto a surface of a substrate, drying the coated substrate and then subjecting it to insolubilization.

The colloidal dispersion used in this invention means a dispersion of colloidal paticles having fine particle size of 0.5 $\mu$m or less and hence the particles are hardly precipitated in the dispersion.

The hydroxyapatite used for preparing the colloidal dispersion in this invention is not specified but may be any conventional product which can be prepared by a conventional method, such as wet process or dry process, among which the wet process is preferable because a product having fine particle size can easily be obtained. Particularly, the product prepared by a wet process is more preferably used without drying after filtering and washing with water because undesirable production of agglomerated particles is inhibited.

The hydroxyapatite in the dispersion has a particle size of 0.5 μm or less, preferably 0.01 to 0.2 μm. When the particle size of hydroxyapatite in the dispersion is over 0.5 μm, the formed coating film has undesirably too large thickness and hence is easily peeled off from the substrate. On the other hand, the lower limit of particle size is not particularly specified, but hydroxyapatite having a particle size of less than 0.001 μm is hardly obtainable, and such a dispersion is unpractical.

In order to prepare a dispersion of hydroxyapatite having a particle size of not more than 0.5 μm, the dispersion prepared by dispersing hydroxyapatite in a dispersion medium is allowed to stand for spontaneous precipitation of particles or is centrifuged, and thereby, the particles having a large particle size are removed off. By this method, any contamination of particles having unexpectedly large particle size can effectively be removed.

The colloidal dispersion of hydroxyapatite can be prepared by a conventional method, for example, by adding fine particles of hydroxyapatite to a dispersion medium and stirring the mixture. The dispersion medium is preferably a medium which is easily evaporated and includes water, alcohols (e.g. ethanol, etc.), and ketones (e.g. methyl ethyl ketone, etc.), among which water is more preferable.

The colloidal dispersion may optionally be incorporated with a dispersing agent in order to deflocculate the agglomerated particles in the dispersion and further may optionally be incorporated with a thickner in order to adjust the viscosity of liquor. The dispersing agent is preferably anionic surfactants such as polycarboxylates (e.g. ammonium polycarboxylate, etc.). The thickner is preferably polyoxyethylene, polyacrylamide, and the like. Besides, the deflocculation of the agglomerated particles may also be effected by treating the dispersion with ultrasonic, homogenizer, emulsifier, etc. during the steps of stirring and/or mixing.

The colloidal dispersion has a concentration of hydroxyapatite of 0.001 to 40% by weight, preferably 0.01 to 20% by weight.

In this invention, when it is desired to obtain a hydroxyapatite-coated thin film having a thickness of 2 μm or less and having a strong adhesion force to the substrate, there is used a colloidal dispersion having a concentration of hydroxyapatite of 0.001 to 1% by weight, preferably 0.01 to 0.5% by weight. When the concentration of hydroxyapatite is less than 0.001% by weight, the liquid film has unpractically too large thickness. On the other hand, when it is desired to obtain a hydroxyapatite-coated film having a relatively thick thickness as 2 μm or more, there is used a colloidal dispersion having a concentration of hydroxyapatite of 1 to 40% by weight, preferably 1 to 20% by weight, more preferably 1 to 10% by weight. When the concentration exceeds 40% by weight, the colloidal dispersion is hardly prepared. When the thickness of formed film exceeds 2 μm, the strength of the coated film becomes lower in proportion to the thickness of the film and the film is sometimes peeled off from the substrate. However, a part of the film is remained on the coated surface of the substrate, and the remaining film adheres to the substrate strongly. Accordingly, when the film having a high strength is required, it is desirable to use a coating liquor having a concentration of hydroxyapatite of 0.001 to 1% by weight. On the other hand, when the formed film is used for some utilities for which the relatively thick film is required, or in which the formed film is not necessarily required to have so high strength, it is desirable to use a coating liquor having a concentration of hydroxyapatite of 1 to 40% by weight.

The colloidal dispersion used in this invention may also be in the form of a hydrosol. The hydrosol as a coating liquor can be preferably used for forming a hydroxy-apatite thin film having a thickness of 2 μm or less.

The hydrosol used in this invention is prepared by mixing an aqueous solution of calcium hydroxide and an aqueous solution of phosphoric acid in a ratio of Ca/P=1.50–2.0 (atomic ratio) in the presence of a protective colloid. Hydrosol contains usually particles having a smaller particle size than that of particles in emulsions or suspensions and the particle size of particles in hydrosol is usually in the range of 0.1 to 0.001 μm.

Methods for preparing hydrosols of hydroxyapatite are disclosed in Gmelins Handbuch der Anorganischen Chemie, Vol. 28, No. B-3, 1158–1159 (1961) as follows.

(i) An aqueous solution of phosphoric acid and an aqueous solution of calcium hydroxide are mixed and the resulting precipitates are stirred with the mother liquor to give a hydrosol of hydroxyapatite.

(ii) An aqueous solution of phosphoric acid and an aqueous solution of calcium hydroxide are mixed in a ratio of Ca/P=1.50 and the resulting precipitates of calcium phosphate are subjected to double decomposition to give a hydrosol of hydroxyapatite.

(iii) An aqueous solution of sodium phosphate is added to an aqueous solution of calcium chloride in the presence of gelatine and the resulting precipitates of calcium phosphate are used for preparing a hydrosol of hydroxyapatite, wherein the properties of the product is dependent on the concentrations of calcium phosphate and gelatine.

According to the experiments of the present inventors, however, the above methods (i) and (ii) could hardly be repeated because the precipitates thus prepared could not be converted into sol even by continuously stirring unless any protective colloid such as gelatine is added thereto. Besides, although the above method (iii) could give a sol, it is contaminated by by-product such as sodium chloride, and owing to the large crystals of contaminated sodium chloride, the hydrosol could not give a coating film having excellent properties when it is coated onto a surface of a substrate.

The improved hydrosol of this invention is prepared by mixing an aqueous solution of calcium hydroxide and an aqueous solution of phosphoric acid in a ratio of Ca/P= 1.50–2.0 (atomic ratio), preferably Ca/P=1.-50–1.67, in the presence of a protective colloid. When the ratio of Ca/P is less than 1.50, there is produced secondary calcium phosphate and hence hydroxyapatite is not produced. Besides, when the ratio of Ca/P is over 2.0, too much amount of unreacted calcium hydroxide is remained, which results disadvantageously in less production of hydroxyapatite.

When an aqueous solution of calcium hydroxide is mixed with an aqueous solution of phosphoric acid in the ratio of Ca/P=1.50–1.67, the mother liquor has a final pH range of 6–8, and on the other hand, when both aqueous solutions are mixed in the ratio of Ca/P of more than 1.67, unreacted calcium hydroxide is remained in the mother liquor and hence, even after completion of the reaction, the mother liquor has a final pH range of 8-11. In this case, the mixture may optionally be neutralized with an acid (e.g. nitric acid, acetic acid, etc.).

Besides, when an aqueous solution of calcium hydroxide is mixed with an aqueous solution of phosphoric acid in the ratio of Ca/P=1.50-1.67, the produced calcium phosphate is remained in the mother liquor at the first stage of the reaction, and when the reaction mixture is stirred or is kept without stirring, the calcium hydroxide retained in the mother liquor is gradually consumed and thereby the Ca/P value of the calcium phosphate increases, which results in lowering of pH value of the mother liquor. When the pH value of the mother liquor becomes in the range of 6-8, most calcium hydroxide is consumed and the double decomposition reaction is completed, and at this stage, the ratio of Ca/P of calcium phosphate becomes equal to that of the starting mixture. When the particles are recovered from the mother liquor and air-dried, it is confirmed by X-ray diffractomery that the particles are low crystalline hydroxyapatite.

The calcium hydroxide used in this invention is not specified but may be any conventional product which can be prepared by a conventional method. The concentration of calcium hydroxide in the aqueous solution is not specified either if it is within the solubility thereof in water, but it is preferably in about 1/100 or more of the solubility thereof in water in order to prevent forming of too thin coating film of hydroxyapatite. The phosphoric acid used in this invention is not specified either but may be any conventional product which can be prepared by a conventional method. The concentration of phosphoric acid in the aqueous solution is not specified either, but it is preferable to make approximately equal to the concentration of calcium hydroxide.

The protective colloid used in this invention includes conventional materials such as gelatine, albumin, gum arabic, protalbinic acid, or lysalbinic acid, and is selected therefrom the most suitable materials in view of easier insolubilization of the formed hydroxyapatite coating film. The protective colloid may be dissolved in either or both of the aqueous solution of calcium hydroxide and/or the aqueous solution of phosphoric acid. The protective colloid is preferably used in a concentration of 0.5 to 10 times by weight of the concentration of the produced hydroxy-apatite. When the concentration of the protective colloid is over 10 times by weight of that of the produced hydroxy-apatite, the hydroxyapatite in the coating film is diluted and shows lower concentration, and hence, the desired continued coating film of hydroxyapatite is hardly obtainable. On the other hand, when the concentration of the protective colloid is lower than 0.5 time by weight, the effect of the protective colloid is less exhibited and hence the desired hydrosol is hardly formed.

The colloidal dispersion can be coated onto the surface of a substrate by a conventional coating method, such as coating, spraying, dipping, and the like.

The substrate used in this invention includes any conventional substrate such as metals, ceramics, glass, and the like. However, when the substrate is a hydrophobic substance such as plastics, the coating is hardly applicable, and hence, it is preferable to subject the substance to surface treatment so as to make the surface hydrophilic.

The method of this invention can also be applied to a substrate having complicated shape of surface, for example, to implants having porous surface, such as implants made from metals (e.g. titanium alloy), ceramics (e.g. alumina ceramics), glass materials (e.g. bioglass material).

The substrate coated with the colloidal dispersion is dried and then subjected to insolubization treatment.

The insolubilization treatment is done for increasing the strength of the hydroxyapatite coating film. The insolubilization is carried out by treating the coated substrate with an insolubilizing agent such as crosslinking agents (e.g. formaldehyde, glutaraldehyde, tannic acid, etc.), more specifically coating or spraying one or more of these agents to the coated substrate. Alternatively, the insolubilization can be done by calcination, whereby the solvent or protecting colloid is removed to remain only the coating film. When the calcination is applied, the solvent or protective colloid should be selected from the substances which do not give any residue by the calcination. The calcination is carried out under suitable conditions which are determined under taking into consideration various factors, such as calcining temperature of the protecting colloid, the dispersing medium and the dispersing agent and further heat resistance of the substrate. Specifically, the calcination temperature is in the range of 100° to 1,200° C., preferably 800° to 1,000° C. When the calcination temperature is lower than 100° C., the hydroxyapatite coating film is insufficiently adhered to the substrate, and on the other hand, when the calcination temperature is higher than 1,200° C., hydroxyapatite is undesirably remarkedly decomposed with heat. The period of calcination is not specified and it may be done until the substrate coated with the hydrosol or colloidal dispersion reaches to the desired temperature, for example, for 5 minutes to 2 hours.

According to this invention, the hydroxyapatite coating film can be formed with stronger adhesion force and can be formed more easily even in case of a substrate having complicated surface in comparison with the known coating method.

Moreover, the method of this invention can be applied to a substrate having a large area more rapidly with lower cost than the known method. The coated substrate prepared by this invention can be used in a variety of utilities, particularly as an implant material, adsorbing and separating agent, and catalyst.

This invention is illustrated by the following Examples and Reference Examples but should not be construed to be limited thereto. In these examples, % means % by weight unless specified otherwise.

EXAMPLE 1

In a 0.055% aqueous solution of calcium hydroxide (500 g) was dissolved purified gelatine (1.0 g), and thereto was added a 0.060% aqueous solution of phosphoric acid (365 g) with stirring over a period of 4 hours (Ca/P=1.66). The pH of the mixture lowered from the initial value of 12.3 to 11.2, and when the mixture was allowed to stand for 7 days, the pH further lowered to 8.0. As a result, the precipitates disappeared to produce a hydrosol.

A part of the hydrosol was taken out and thereto was added sodium sulfate (a kind of agglomerating agent), and the agglomerated product was separated by filtration. The resulting slurry was air-dried and the powder was analyzed by X-ray diffractomery. As a result, the product was low crystalline hydroxyapatite as shown in the accompanying FIG. 1.

As a substrate, there was used an alumina dense sintered product (purity 99.9%) (length 40 mm, width 40 mm, thickness 5 mm) having a concave (length 25 mm, width 25 mm, depth 1 mm), wherein a single layer of alumina beads (diameter 1 mm) was bonded in said concave.

The above hydrosol as a coating liquor was added onto the substrate until the concave was completely filled with the hydrosol, and the resultant was air-dried and then calcined with raising the temperature from room temperature to 800° C. with raising rate of 100° C./hour and was kept at 800° C. for one hour.

The coating film thus calcined showed gloss and interference band. When measured with a film thickness meter, the coating film had a thickness of about 0.3 $\mu$m.

When the substrate thus prepared was dipped in a physiological saline solution for one week, the coating film was kept rigidly without change.

EXAMPLE 2

In the same manner as described in Example 1 by using the same reagents as used in Example 1 except that a 0.060% aqueous solution of phosphoric acid (405 g) was used, there was prepared a hydrosol having Ca/P=1.50. During the preparation, the pH lowered from the initial one of 12.3 to to 10.8, and when the mixture was allowed to stand for 7 days, the pH lowered to 8.0. As a result, the hydrosol was prepared without any precipitation.

When the hydrosol thus prepared was tested in the same manner as in Example 1, it was confirmed that it was low crystalline hydroxyapatite.

As a substrate, there was used an alumina substrate having a surface roughness Ra=0.05 $\mu$m (purity 99.9%, length 10 mm, width 10 mm, thickness 0.8 mm) which was washed with acetone.

The above hydrosol as a coating liquor was dropped onto the surface of the alumina substrate to form a liquid film (thickness 1 mm). This coated substrate was air-dried and calcined in the same manner and under the same conditions as in Example 1.

The coating film thus calcined showed gloss and interference band like the product in Example 1. When measured with a film thickness meter, the coating film had a thickness of about 0.3 $\mu$m.

When the substrate thus prepared was dipped in a physiological saline solution for one week like in Example 1, the coating film was kept rigidly without change.

EXAMPLE 3

By using coating liquor and alumina dense sintered product as used in Example 1, the sintered product was filled with the hydrosol in the concave and air-dried.

The sintered product thus treated was subsequently insolubilized by dipping in a 5% glutaraldehyde solution for 20 hours.

When the sintered product thus prepared was dipped in a physiological saline solution for one week like in Example 1, the coating film was kept rigidly without change.

EXAMPLE 4

As a substrate, there was used a titanium plate having a surface roughness Ra=0.2 $\mu$m (JIS second degree, length 10 mm, width 10 mm, thickness 1 mm) which was washed with acetone.

The coating liquor as used in Example 1 was dropped onto the surface of the titanium plate to form a liquid film (thickness 1 mm). The product thus prepared was air-dried and calcined in the same manner and under the same conditions as in Example 1.

The coating film thus calcined showed gloss and interference band like the product in Example 1. When measured with a film thickness meter, the coating film had a thickness of about 0.3 $\mu$m.

When the titanium plate thus prepared was dipped in a physiological saline solution for one week in the same manner as in Example 1, the coating film was kept rigidly without change.

REFERENCE EXAMPLE 1

Hydroxyapatite (not calcined) (0.50 g), which was prepared by mixing an aqueous solution of secondary ammonium phosphate and an aqueous solution of calcium nitrate, was added to a 0.1% aqueous solution of gelatine (1000 g) and the mixture was stirred for one day. As a result, the product was wholly precipitated. The mixture was stirred again and filled into the concave of an alumina dense sintered product as used in Example 1, and the substrate thus treated was air-dried to form a white coating film. The product was subsequently calcined under the same conditions as in Example 1. As a result, the coating film was easily peeled off from the substrate only by touch with finger.

REFERENCE EXAMPLE 3

In the same manner as in Example 1 except that no gelatine was used, there were mixed an aqeuous solution of calcium hydroxide and an aqueous solution of phosphoric acid, both having the same concentration and the same amount as in Example 1. As a result, the mixture showed similar change of pH value to that in Example 1, but immediately after mixing, precipitates were produced and hydrosol could not be produced.

The precipitates were separated by filtration and air-dried, and the particles thus obtained were measured by X-ray diffractometry. As a result, it showed the same pattern as in FIG. 1, and hence, it was confirmed that the product is also low crystalline hydroxyapatite.

By using as a substrate the same alumina dense sintered product as used in Example 1, the above precipitates were filled in the concave of the sintered product, and the substrate thus obtained was air-dried and calcined in the same manner and under the same conditions as in Example 1.

The coating film thus formed was easily peeled off only by touch with finger.

REFERENCE EXAMPLE 3

In the same manner as described in Example 1 by using the same reagents as used in Example 1 except that a 0.060% aqueous solution of phosphoric acid (434 g) was used, there was prepared a hydrosol having Ca/P=1.40. A part of the hydrosol thus prepared was taken and thereto was added sodium sulfate (agglomerating agent) and the agglomerated product was separated by filtration. The slurry thus obtained was air-dried and the powder was measured by X-ray diffractometry in the same manner as in Example 1. As a result, the product was a mixture of low crystalline hydroxyapatite and secondary calcium phosphate.

REFERENCE EXAMPLE 4

In the same manner as described in Example 1 by using the same reagents as used in Example 1 except that a 0.060% aqueous solution of phosphoric acid (243 g) was used, there was prepared a hydrosol having Ca/P=2.50. A part of the hydrosol thus prepared was taken and thereto was added sodium sulfate (agglomerating agent) and the agglomerated product was separated by filtration. The slurry thus obtained was air-dried and the powder was measured by X-ray diffractometry in the same manner as in Example 1. As a result, the product was a mixture of low crystalline hydroxyapatite and low crystalline calcium hydroxide.

EXAMPLE 5

To a 0.555M calcium nitrate (0.6 liter, pH=10) was added dropwise a 0.167M secondary ammonium phosphate (1.2 liter, pH=10), and the mixture was boiled for one hour and thereafter the precipitates were separated by filtration and washed with water. To the precipitates thus obtained was added ammonium polycarboxylate (SN-EX5468 30% solution, manufactured by San Nopco K.K.) (3.0 g), and the mixture was stirred to give a slurry containing 19.5% of hydroxyapatite.

The slurry thus obtained was diluted with water in 100 folds, and the diluted slurry (100 ml) was added to a glass beaker (diameter 60 mm) and subjected to deflocculation with ultrasonic for 4 hours and thereafter allowed to stand for 21 days.

The liquid of 7 mm in depth from the liquid surface was taken and analyzed. As a result, the colloidal dispersion had a particle size of less than 0.1 $\mu$m and a concentration of 0.06%.

As a substrate, there was used an alumina substrate having a surface roughness Ra=0.05 $\mu$m (purity 99.9%, length 10 mm, width 10 mm, thickness 0.8 mm) which was washed with acetone.

The colloidal dispersion as a coating liquor prepared above was dropped onto the surface of the alumina substrate to form a liquid film (thickness 1 mm), and the substrate thus treated was air-dried and calcined by raising the temperature from room temperature till 800° C. with raising rate of 100° C./hour and keeping at 800° C. for one hour.

When observed with a scanning electron microscope (hereinafter referred to "SEM"), a coating film (thickness about 1 $\mu$m) was formed on the alumina substrate, and the hydroxyapatite had a particle size of about 0.1 $\mu$m.

The coating film on the substrate was subjected to an adhesion test (by the method described in JIS K5400, K5980), that is, the coating film was cross-cut with a cutter knife with six lines each in longitudinal and transversal directions at intervals of each 1 mm, and thereon a cellophane tape was adhered, and then, the tape was rapidly peeled off. As a result, no peeling of the coating film was observed.

Besides, when the product prepared by air-drying the slurry containing 19.5% of hydroxyapatite, followed by calcining at 800° C. as prepared above was analysed by X-ray diffractometry, the product was composed of only hydroxy-apatite.

EXAMPLE 6

As a substrate, there was used an alumina dense sintered product (purity 99.9%) (length 40 mm, width 40 mm, thickness 5 mm) having a concave (length 25 mm, width 25 mm, depth 1 mm), wherein a single layer of alumina beads (diameter 1 mm) was bonded in said concave.

The same coating liquor as used for dropping onto the substrate in Example 5 was added onto the substrate until the concave was completely filled with the colloidal dispersion, and the resultant was air-dried and then calcined in the same manner as in Example 5.

When observed with SEM, it was confirmed that a coating film of hydroxyapatite was formed on the surface of the alumina dense sintered product.

EXAMPLE 7

The slurry containing 19.5% of hydroxyapatite as prepared in Example 5 was diluted with water in 4 folds and subjected to deflocculation with ultrasonic for 11 hours, and the deflocculated product was taken in a glass tube (diameter 12 mm) in a height of liquid of 45 mm and centrifuged at 3,000 r.p.m. for 45 minutes.

The liquid of 35 mm in depth from the liquid surface was taken and analyzed. As a result, the colloidal dispersion had a particle size of less than 0.1 $\mu$m and a concentration of 0.03%.

As a substrate, there was used as the same alumina substrate as used in Example 5. The colloidal dispersion as prepared above was dropped onto the substrate in the same manner as in Example 5 to form a liquid film (thickness 1 mm), and the substrate thus treated was sir-dried and calcined under the same conditions as in Example 5.

When observed with SEM, a coating film (thickness about 1 $\mu$m) was formed on the alumina substrate and the hydroxyapatite had a particle size of about 0.1 $\mu$m.

Besides, the coated substrate was subjected to an adhesion test in the same manner as in Example 5, and as a result, any peeling of the coating film was entirely not observed.

EXAMPLE 8

The slurry containing 19.5% of hydroxyapatite as prepared in Example 5 was diluted with water in 100 folds and subjected to deflocculation with ultrasonic for 4 hours, and the deflocculated product (100 ml) was taken in a glass beaker (diameter 60 mm) and allowed to stand for 100 hours.

The liquid of 35 mm in depth from the liquid surface was taken and analyzed. As a result, the colloidal dispersion had a particle size of less than 0.3 $\mu$m and a concentration of 0.15%.

As a substrate, there was used the same alumina substrate as used in Example 5. The colloidal dispersion as prepared above was dropped onto the substrate in the same manner as in Example 5 to form a liquid film (thickness 1 mm), and the substrate thus treated was air-dried and calcined under the same conditions as in Example 5.

When observed with SEM, a coating film (thickness about 1 $\mu$m) was formed on the alumina substrate, and the hydroxyapatite had a particle size of about 0.1 $\mu$m.

Besides, the coated substrate was subjected to an adhesion test in the same manner as in Example 5, and as a result, any peeling of the coating film was entirely not observed.

REFERENCE EXAMPLE 5

The slurry containing 19.5% of hydroxyapatite as prepared in Example 5 was diluted with water in 300 folds and subjected to deflocculation with ultrasonic for 4 hours. The deflocculated product was analyzed likewise. As a result, the liquid had a particle size of less than 3 $\mu$m (average particle size 0.5 $\mu$m) and a concentration of 0.06%.

As a substrate, there was used the same alumina substrate as used in Example 5. The dispersion as prepared above was dropped onto the substrate in the same manner as in Example 5 to form a liquid film (thickness 1 mm), and the substrate thus treated was air-dried and calcined under the same conditions as in Example 5.

When observed with SEM, a coating film (thickness about 3 μm) was formed on the alumina substrate, and the hydroxyapatite had a particle size of about 1 μm.

Besides, the coated substrate was subjected to an adhesion test in the same manner as in Example 5, and as a result, the coating film was peeled off.

EXAMPLE 9

The slurry containing 19.5% of hydroxyapatite as prepared in Example 5 was diluted with water in 2 folds and subjected to deflocculation with ultrasonic for 11 hours, and the deflocculated product (100 ml) was taken in a glass beaker (diameter 60 mm) and allowed to stand for 100 hours.

The liquid of 35 mm in depth from the liquid surface was taken and analyzed. As a result, the dispersion had a particle size of less than 0.3 μm and a concentration of 2.0%.

As a substrate, there was used the same alumina substrate as used in Example 5. The dispersion as prepared above was dropped onto the substrate in the same manner as in Example 5 to form a liquid film (thickness 1 mm), and the substrate thus treated was air-dried and calcined under the same conditions as in Example 5.

When observed with SEM, a coating film (thickness about 3 μm) was formed on the alumina substrate, and the hydroxyapatite had a particle size of about 0.3 μm.

Besides, the coated substrate was subjected to an adhesion test in the same manner as in Example 5, and as a result, the coating film was peeled off. However, when the peeled portion was observed with SEM, a very thin hydroxy-apatite film remained on all of the surface of the peeled portion.

EXAMPLE 10

To a 0.555M calcium nitrate (0.6 liter, pH=10) was added dropwise a 0.167M secondary ammonium phosphate (1.2 liter, pH=10), and the mixture was boiled for one hour and thereafter the precipitates were separated by filtration, washed with water and then lyophilized to give powder of hydroxyapatite.

The powder (2.0 g) was added to a glass beaker (diameter 60 mm) containing water (98 ml), and thereto was added a dispersing agent ammonium polycarboxylate (SN-EX5468 30% solution, manufactured by San Nopco K.K.) (0.2 g), and the mixture was subjected to deflocculation with ultrasonic for 4 hours and thereafter allowed to stand for 21 days.

The liquid of 7 mm in depth from the liquid surface was taken and analyzed. As a result, the colloidal dispersion had a particle size of less than 0.1 μm and a concentration of 0.04%.

As a substrate, there was used the same alumina substrate as used in Example 5. The colloidal dispersion as a coating liquor prepared above was dropped onto the substrate in the same manner as in Example 5 to form a liquid film (thickness 1 mm), and the substrate thus treated was air-dried and calcined under the same conditions as in Example 5.

When observed with SEM, a coating film (thickness about 1 μm) was formed on the alumina substrate, and the hydroxyapatite had a particle size of about 0.1 μm.

Besides, the coated substrate was subjected to an adhesion test in the same manner as in Example 5, and as a result, no peeling of the coating film was observed.

EXAMPLE 11

The slurry containing 19.5% of hydroxyapatite as prepared in Example 5 was diluted with water in 3 folds and subjected to deflocculation with ultrasonic for 26 hours, and the deflocculated product was taken in a glass tube (diameter 12 mm) in a height of liquid of 45 mm and centrifuged at 3,000 r.p.m. for 45 minutes.

The liquid of 35 mm in depth from the liquid surface was taken and analyzed. As a result, the colloidal dispersion had a particle size of less than 0.1 μm and a concentration of 5.29%.

Polyoxyethylene (PEO-18, manufactured by Seitetsu Kagaku Kogyo, Ltd.) (0.06 g) was dissolved in the colloidal dispersion (10 g) to obtain a coating liquor.

As a substrate, there was used as the same alumina substrate as used in Example 6. The coating liquor as prepared above was added onto the substrate until the concave was completely filled with the coating liquor, and the resultant was air-dried and then calcined in the same manner as in Example 6.

When observed with SEM, it was confirmed that a coating film of hydroxyapatite was formed on the surface of the aluminum dense sintered product.

What is claimed is:

1. A method for forming a hydroxyapatite coating film which has a thickness of less than 2 microns on a surface of a substrate, which comprises coating a coating liquor comprising a colloidal dispersion of hydroxyapatite having a fine particle size of from 0.01 to 0.2 μm onto a surface of a substrate, drying the coated substrate and then subjecting it to insolubilization.

2. The method according to claim 1, wherein the coating of the coating liquor is carried out with a hydrosol prepared by mixing an aqueous solution of calcium hydroxide and an aqueous solution of phosphoric acid in an atomic ratio of Ca/P=1.50–2.0 in the presence of a protective colloid.

3. The method according to claim 2, wherein the hydrosol is prepared by mixing an aqueous solution of calcium hydroxide and an aqueous solution of phosphoric acid in an atomic ratio of Ca/P=1.50–1.67.

4. The method according to claim 1, wherein the coating of the coating liquor is carried out with a colloidal dispersion containing 0.001 to 40% by weight of a hydroxyapatite.

5. The method according to claim 4, wherein the colloidal dispersion has a particle size of the hydroxyapatite of 0.01 to 0.2 μm.

6. The method according to claim 4, wherein the insolubilization is carried out by calcining at a temperature of 100° to 1200° C. for 5 minutes to 2 hours.

* * * * *